United States Patent [19]

Ingram

[11] 4,320,343
[45] Mar. 16, 1982

[54] SAFETY VALVE FOR EXPOSING A MEASURING PROBE TO A FLUID

[75] Inventor: Maxwell Ingram, Hackensack, N.J.

[73] Assignee: Marine Electric Corporation, Brooklyn, N.Y.

[21] Appl. No.: 81,030

[22] Filed: Oct. 1, 1979

[51] Int. Cl.³ ............................................. G01N 27/28
[52] U.S. Cl. .................................................... 324/450
[58] Field of Search ...................... 324/450, 65 P, 61 P

[56] References Cited

U.S. PATENT DOCUMENTS 2,832,039   4/1958   Hardesty ............................. 324/450
2,985,821   5/1961   Del Chiocca ....................... 324/450

Primary Examiner—Stanley T. Krawczewicz
Attorney, Agent, or Firm—Wender, Murase & White

[57] ABSTRACT

A safety valve for exposing a measuring probe to a fluid comprising a hollow inner valve body with a valve seat movably positioned within a hollow outer valve body having a cooperating valve element for providing fluid-tight engagement when the valve is closed. The inner valve body partially extends from the outer valve body when the valve is open for passage of the fluid into an inner chamber for exposing the inserted probe to the fluid. The probe is secured to the inner valve body by a threaded cap, the movement of which is translated to the inner valve body in the presence of the probe for moving the inner valve body to the open valve position. The valve is prevented from being opened in the absence of the probe by a spring mounted on the outer valve body engaging a catch on the cap for restricting movement thereof preventing the valve from being opened. The valve is latched in the open and closed positions by a Z-shaped slot in the inner valve body cooperating with a guide pin mounted on the outer valve body. The spring further engages a catch in the cap when the inner valve body is in the open position for restricting probe-releasing movement of the cap thereby preventing removal of the probe while the valve is open.

19 Claims, 7 Drawing Figures

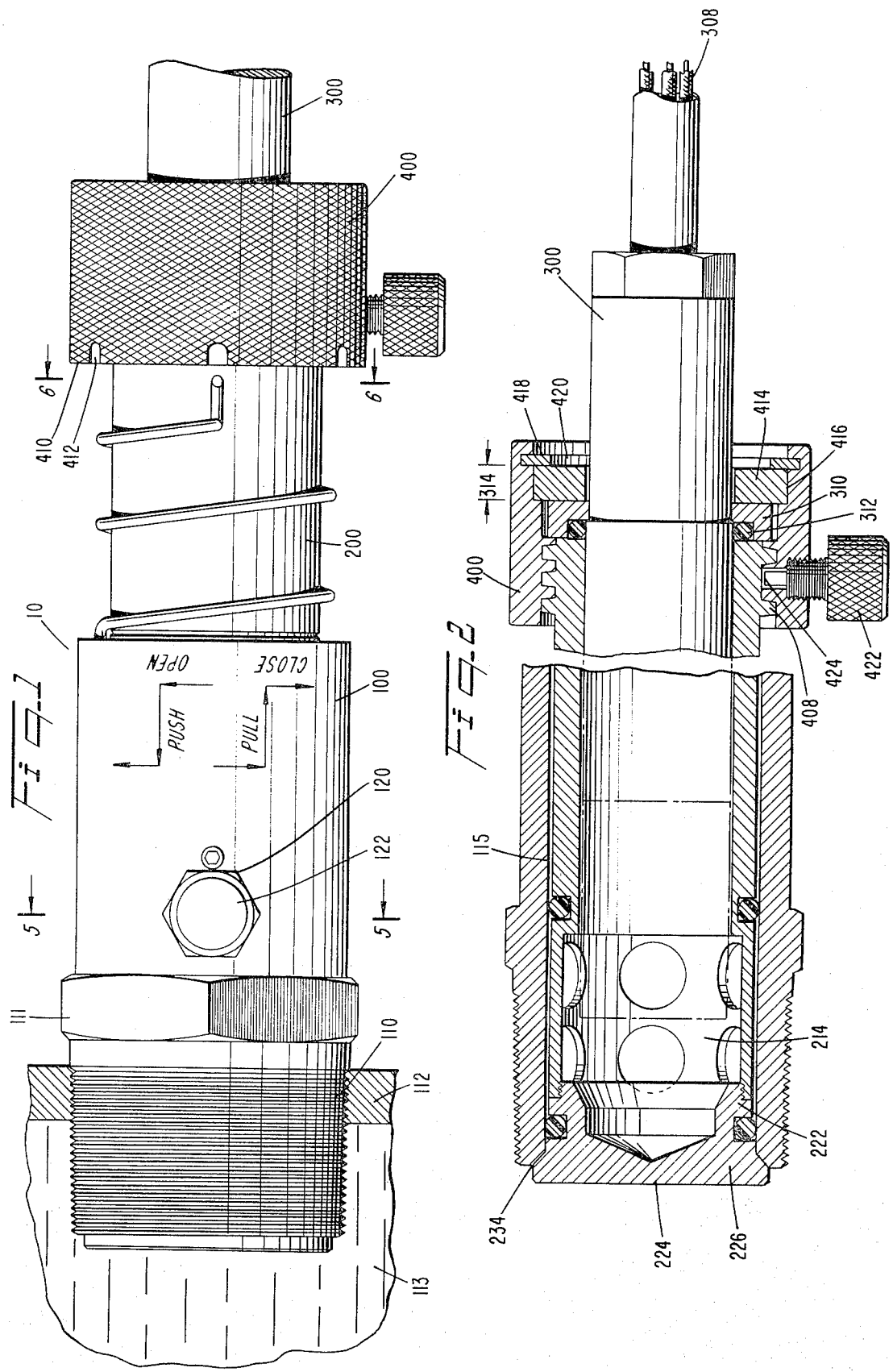

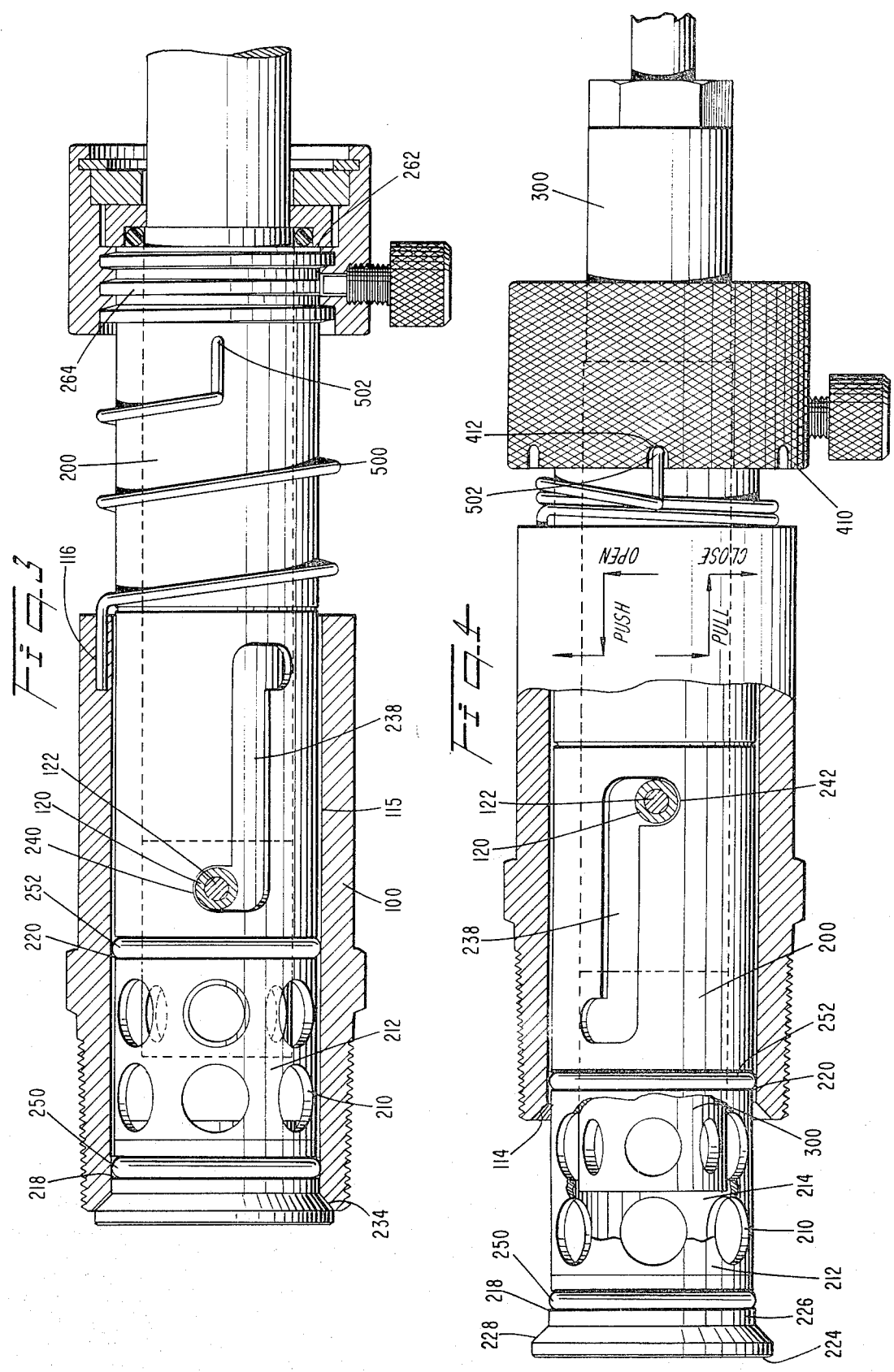

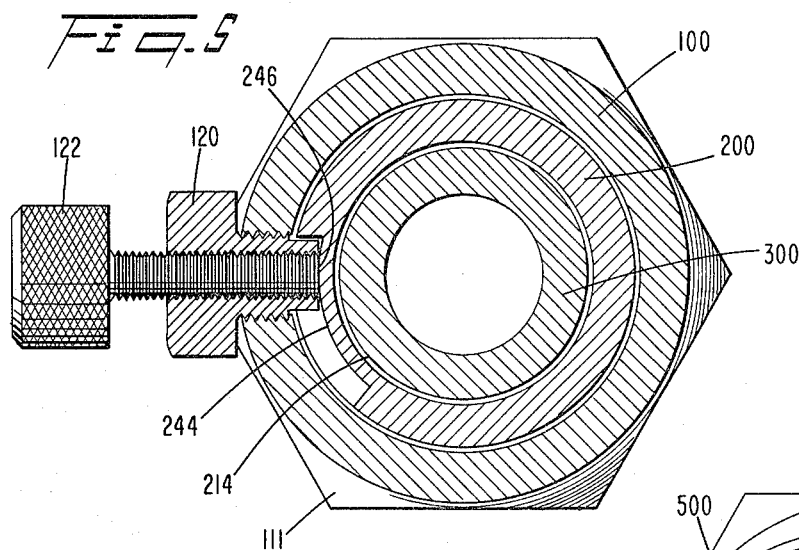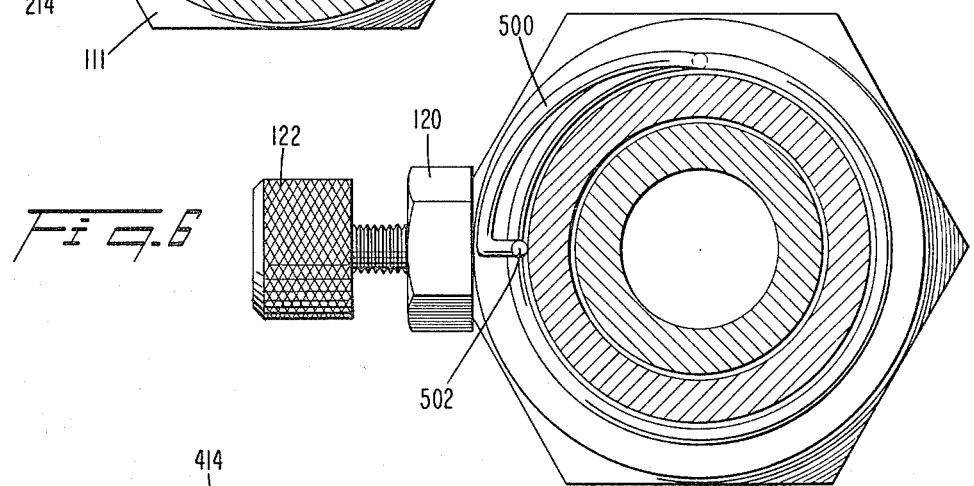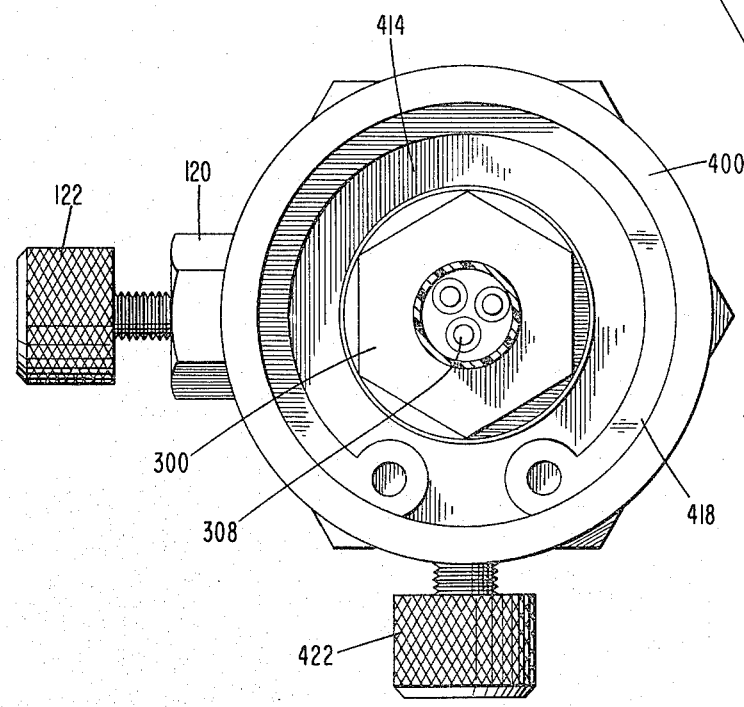

SAFETY VALVE FOR EXPOSING A MEASURING PROBE TO A FLUID

BACKGROUND OF THE INVENTION

1. Field of the Invention

This invention relates to safety valves, and in particular to valves for exposing to a fluid a probe, such as a coaxial salinity cell employed in measuring the conductivity of a pressurized electrolyte solution.

2. Description of the Prior Art

Conventional coaxial-type valves presently in use with probes, such as salinity cells, typically utilize a gate valve configuration having a rising stem and valve handle. The conventional type of valve presents a number of disadvantages. Conventional gate valves require a significant clearance area for cell withdrawal, and further pose the possibility of crushing the cell or probe in the gate valve when closing the gate. Such valves also require packing and repacking around the rising valve stem to prevent leakage.

In pressurized systems using conventional coaxial valves, there is also a danger that the interior of the valve can be accidentally blown out due to the pressure, creating a hazard to the users. In addition, when the valve is in the open position, it is possible for the operator to inadvertently remove the probe from the valve, resulting in injury to the operator from escaping fluid as well as causing damage to the surrounding locations. Furthermore, it is possible to inadvertently open the valve when the probe is missing, again causing injury and damage. In addition, if left partially open by accident, such a valve remains open similarly resulting in injury and flooding.

SUMMARY OF THE INVENTION

It is an object of the present invention to construct a safety valve which, if partially left open, automatically closes to prevent pressurized fluid from escaping.

It is another object to effect improved sealing of the valve at higher pressures in order to ensure there is no fluid leakage.

Furthermore, it is an object of the present invention that the inner portion of the valve be prevented from being expelled by the pressure to avoid possible injuries, flooding, and loss of fluid.

The present invention has an object to construct a valve which automatically closes if an attempt is made to remove the probe while the valve is open.

It is an object of the present invention to prevent the operator from opening the valve should the operator fail to first reinstall a probe into the valve. Another object is to construct a valve in which the probe or cell assembly cannot be removed from the valve if the valve remains open.

A further object is that the valve include much simpler components and smaller space requirements than a conventional valve, and that operation of the valve not crush the probe. Finally, it is an object that the valve be simple and efficient to use, yet offer improved reliability and safety.

Further objects of the present invention will become apparent in the full description of the invention and drawings set forth below.

The safety valve for exposing a measuring probe to a fluid comprises a hollow cylindrical outer valve body having a valve seat, and a hollow inner valve body movably positioned coaxially in the outer valve body having a valve element for cooperation with the valve seat. The inner valve body has a base defining an interior chamber being open at one end for receiving a probe, and further has apertures in the cylinder wall adjacent the base for fluid passage into the chamber. The inner valve body partially extends from the outer valve body in the open valve position permitting passage of the fluid into the chamber for exposing the probe to the fluid, and the valve seat engages the valve element in the closed valve position for providing a fluid-tight engagement blocking passage of fluid into the chamber. Coupled with the inner valve body is a cap movable in a first direction for securing the probe in the inner valve body, and a second direction for releasing the probe. In the absence of the probe, the valve is prevented from being opened by a spring mounted on the outer valve body engaging a catch on the cap for restricting movement of the cap and preventing the inner valve body from moving to the open position. The spring also engages a catch in the cap when the valve is in the fully open position, restricting movement of the cap in the second direction for preventing removal of the probe when the valve is open. The valve is latched in open and closed positions by a Z-shaped slot in the inner valve body cooperating with a guide pin mounted on the outer valve body.

BRIEF DESCRIPTION OF THE DRAWINGS

FIG. 1 is an elevated plan view of one embodiment of a safety valve for exposing a measuring probe to a fluid, in the closed position, threaded into a fluid container and having an inserted probe in accordance with the present invention;

FIG. 2 is a partially cut away longitudinal sectional view of one embodiment of the valve showing the inserted probe in accordance with the present invention;

FIG. 3 is a longitudinal sectional view of one embodiment of the outer valve body and cap with the inner valve body in a closed valve position in accordance with the present invention, FIG. 4 is a partially cut away plan view of one embodiment of the valve showing the inner valve body in the open position in accordance with the present invention;

FIG. 5 is a sectional view along line 5—5 of FIG. 1 showing one embodiment of a guide pin engaging a slot in the inner valve body in accordance with the present invention;

FIG. 6 is a sectional view along line 6—6 of FIG. 1 illustrating one embodiment of a spring used in the valve according to the present invention, and FIG. 7 is an end view of the valve showing one embodiment of the inserted probe being held in place by the cap in accordance with the present invention.

DESCRIPTION OF THE PREFERRED EMBODIMENTS

Referring to FIG. 1, there is shown a safety valve 10, having a hollow cylindrical outer valve body 100 with a threaded end 110 and nut portion 111 threaded into the wall 112 of a pressurized vessel containing a fluid 113, such as hot electrolyte solution. As shown in FIGS. 2-4, the outer valve body has a smooth valve seat 114 located on the inner circumference of the end exposed to the fluid, which is tapered at an appropriate angle, in this case 45 degrees. The outer valve body has an interior surface 115, and a hole 116 in the end opposite the valve seat end. The outer valve body has a guide pin 120, such as a screw shown threaded through the outer valve body wall, which extends into the interior of the outer valve body. There is also included a locking thumb screw 122 for further locking the inner body in the opened or closed valve position as further explained below.

A hollow cylindrical inner valve body 200 is slidably positioned coaxially within the outer valve body. The inner valve body has apertures 210 located in wall portion 212 at one end. The apertures permit passage of the fluid into the hollow interior chamber 214 of the inner valve body when the valve is open. On each end of wall portion 212 are grooves 218 and 220 for mounting "O" rings 250 and 252 therein. A base 222 is threaded into one end of the inner valve body, which has a pressure bearing face 224. The valve base carries a valve element 226 having smooth tapered shoulder 228 on the outer circumference thereof at an angle appropriate for mating with the tapered valve seat 114 of the outer valve body. The shoulder surface cooperates with the corresponding tapered valve seat on the outer valve body for a fluid-tight engagement 234 when the valve is in the closed position.

The inner valve body further has a Z-shaped slot 238 having latching portions 240 and 242. As shown in FIG. 5, the slot has a base 244 and does not extend through to the interior chamber 214 of the inner valve body. The slot is aligned with the guide pin 120 on the outer valve body to guide the rotational and axial movement of the inner valve body within the outer valve body. The pin and slot are arranged so as to provide a certain amount of frictional force therebetween at 246. Furthermore, the valve may be latched in the closed position by the guide member 120 fitting into the latching portion 240 of the Z-shaped slot corresponding to the closed position. The latching portion 242 located at the opposite end of the Z-shaped slot is for latching the valve in the open position. The valve may be locked in either latched position by locking thumb screw 122 bearing on the base 244 of the shallow Z-shaped slot.

The inner valve body further has an end opposite the base being open and having an end abutment surface 262. There is also an externally threaded portion 264 having V-shaped truncated threads.

A cylindrical measuring probe 300, such as a salinity cell assembly for insertion into the valve has leads 308. A spacer portion 310 is positioned on the circumference of the probe. The spacer portion houses an "O" ring 312, and is of a particular thickness 314. The spacer portion permits the probe to be secured within the valve, and provides a fluid-tight seal with the inner valve body.

A cap 400 for securing the measuring probe 300 within the valve is shown threaded onto the inner valve body 200 by means of matching truncated threads 408. The cap has a leading edge 410 having a catch 412, preferrably in the form of notches spaced apart at intervals. A cell clamping disc 414 is held in a slotted portion 416 of the cap by a retaining ring 418 contained within a lip 420 of the cap. The clamping disc abuts the spacer portion and holds it fast against end surface 262 of the inner valve body. The cap further has a slot locking member 422, such as a thumb screw, which has a flat portion 424 for engaging an axial slot in the inner valve body threads.

A resilient opposing member 500, such as a spring, is mounted to the outer valve body at hole 116. The spring has a finger portion 502 at one end which is bent to extend radially outward from the axis of the coaxial valve so that it is engageable with one of the notches 412 on the cap.

In normal operation of opening the closed valve, the cap 400 is mounted on the salinity cell probe 300, with the probe spacer portion 310 engaging the clamping disc 414 being held in place by the retaining ring. The probe is then inserted into the hollow inner valve body chamber, and the cap is threaded thereon by movement in a clockwise direction. Sufficient tightening of the cap onto the inner valve body causes the cap to press the probe spacer portion against the end surface 262 of the inner valve body, thus enabling the cap to be fully tightened. As shown in FIG. 1, during this tightening the notches 412 do not engage the spring finger 502 if the probe is present due to spacer portion 310 limiting travel of the cap. In the fully tightened position, the thumb screw 422 may be tightened into the axial slot at 424 for locking the cap firmly in place. Any further rotational clockwise movement of the cap is then translated to the inner valve body. The guiding movement friction present between the guide pin and Z-shaped slot is then overcome, and the inner valve body may be rotated clockwise enabling the valve to be unlatched from the closed position. The inner valve body containing the probe may then be pressed inward, and then rotated clockwise further to be latched by the guide pin and Z-shaped slot in the open position as shown in FIG. 4. In the valve open position, wall portion 212 of the inner valve body extends out of the outer valve body and is immersed in fluid. The apertures 210 permit the passage of the fluid into the hollow inner chamber of the inner valve body, thus exposing the probe 300 to the fluid. Since the matching tapered faces 114 and 228 are disengaged and no longer provide a seal, "O" ring 252 positioned in groove 220 bearing against the internal wall of the outer valve body serves to seal the fluid within the open valve.

To close the valve, the cap and inner valve body are rotated in the opposite counterclockwise direction, and the inner valve body may be pulled back into the valve, assisted by the force of the expanding spring and the fluid pressure. The inner valve body may then be further rotated counterclockwise and latched in the closed position, as shown in FIG. 3. When the valve is closed, the valve seat and valve element provide a fluid-tight sealing engagement. A second "O" ring 250 positioned in groove 218 may be provided for added sealing protection. Thus, it can be seen that the valve is constructed so that the probe may be removed only while the valve is in the closed position.

In the event the valve is unlatched and left partially open, the pressure of the fluid against the pressure bearing surface 224 of the valve base automatically pushes the inner valve body inward and closes the valve, keeping it closed so long as fluid pressure is exerted against it. Due to the wedge configuration of the valve seat and valve element shoulder, any increase in pressure serves to press the matching taper valve seat and shoulder together even tighter for improved sealing fit.

To attempt to open the valve with the salinity cell probe being absent, the cap must first be threaded clockwise as in normal operation to tighten the cap onto the inner valve body housing. However, since the probe and probe spacer portion 310 is absent, continued tightening of the cap causes it to axially travel permitting one of the notches 412 to catch the spring end finger 502. The flexing and resilient resistance action of the spring 500 restricts movement of the cap, preventing it from being tightened fully onto the inner valve body. Thus, rotational translation of the motion of the cap to the inner valve body is prevented. The inner valve body thus remains latched in the closed position, even when the locking thumb screw 122 has been disengaged. Therefore, the valve cannot be opened when the probe is absent.

When the valve has been locked in the latched open position, the spring also prevents the probe from being inadvertently removed, since the spring finger end 502 engages one of the notches 412 in the cap as shown in FIG. 4. Unthreading rotation of the cap in an attempt to release the probe is restricted by the spring. Thus, removal of the probe is prevented.

It should be noted that the accompanying description and drawings are meant to describe preferred embodiments of the invention, but are not intended to limit the spirit and scope thereof.

What is claimed is:

1. A safety valve for exposing a measuring probe to a fluid, comprising:
    a hollow cylindrical outer valve body having a valve seat at one end;
    a hollow cylindrical inner valve body positioned coaxially within said outer valve body and carrying a valve element at one end for cooperation with said valve seat, said inner valve body being closed at one end by a base so as to define an interior chamber and being open at the opposite end for receiving the probe, the cylindrical wall of said inner valve body adjacent said base having apertures for passage of fluid therethrough;
    said valve element being a tapered shoulder on said one end of said inner valve body and said valve seat being a surface of said outer valve body conforming to said shoulder of said valve element to assure fluid tight engagement therebetween in response to pressure exerted by the fluid on said base of said inner valve body;
    said inner valve body being movable within said outer valve body between open and closed valve positions, said inner valve body extending at least partially from said outer valve body in said open valve position for permitting passage of fluid through said apertures into said chamber for exposing the probe to the fluid, and said valve seat engaging said valve element in said closed valve position for blocking the passage of fluid into said chamber;
    means for securing the probe in said inner valve body, said probe securing means being movable in a first direction for securing the probe and a second direction for releasing the probe; and
    means for closing the valve in response to movement of said probe securing means in said second direction so that said inner valve body moves to said closed position prior to removal of the probe.

2. A valve as defined in claim 1, further comprising means intermediate said probe securing means and said outer valve body for restricting movement of said probe securing means in said second direction when the valve is in said open position.

3. A valve as defined in claim 2, wherein said restricting means includes a catch on said securing means, and further includes means mounted on said outer valve body for engagement with said catch when the valve is in said open position so that movement of said probe securing means in said second direction is restricted, thereby preventing removal when the valve is open.

4. A valve as defined in claim 3, wherein said catch engagement means comprises a coil spring.

5. A valve as defined in claim 3, wherein said probe securing means comprises a hollow cylindrical cap threaded onto said inner valve body; and wherein said catch comprises at least one notch in said cap.

6. A valve as defined in claim 1, further comprising means intermediate said inner and outer valve bodies for latching said inner valve body in said open position, said latching means being releasable in response to movement of said inner valve body in a predetermined direction coincidental with said second direction of movement of said probe securing means.

7. A valve as defined in claim 5, wherein said latching means includes means for latching said inner valve body in said closed valve position.

8. A valve as defined in claim 6, wherein said latching means comprises a Z-shaped slot in said inner valve body and a guide pin mounted on said outer valve body for cooperation with said slot.

9. A valve as defined in claim 1, wherein said valve element comprises a smooth tapered shoulder on said one end of said inner valve body; and wherein said valve seat comprises a tapered surface of said outer valve body conforming to said tapered shoulder of said valve element to assure fluid-tight engagement therebetween in response to pressure exerted by the fluid on the base of said inner valve body.

10. A valve as defined in claim 1, further comprising means connected to said outer valve body for biasing said inner valve body toward said closed valve position.

11. A safety valve for exposing a measuring probe to a fluid, comprising:
    a hollow cylindrical outer valve body having a valve seat at one end;
    a hollow cylindrical inner valve body positioned coaxially within said outer valve body and carrying a valve element at one end for cooperation with said valve seat, said inner valve body being closed at one end by a base so as to define an interior chamber and being open at the opposite end for receiving the probe, the cylindrical wall of said inner valve body adjacent said base having apertures for passage of fluid therethrough;
    said inner valve body being movable within said outer valve body between open and closed valve positions, said inner valve body extending at least partially from said outer valve body in said open valve position for permitting passage of fluid through said apertures into said chamber for exposing the probe to the fluid, and said valve seat engaging said valve element in said closed valve position for blocking the passage of fluid into said chamber;
    means for securing the probe in said inner valve body, said probe securing means being movable in a first direction for securing the probe and a second direction for releasing the probe; and
    lock means in the form of a spring wound around said inner valve body and operatively connected with said probe securing means and said outer valve body for exerting a biasing force preventing the valve from being opened in the absence of the probe.

12. A valve as defined in claim 11, wherein said lock means includes means for latching said inner valve body in said closed position, said latching means being releasable in response to movement of said inner valve body in a predetermined direction.

13. A valve as defined in claim 12, wherein said lock means further includes a catch on said probe securing means, and means mounted on said outer valve body for engagement with said catch in the absence of the probe for preventing movement of said probe securing means in said first direction from moving said inner valve body in said predetermined direction.

14. A valve as defined in claim 13, further comprising means on said probe securing means for cooperation with an inserted probe to prevent engagement of said catch with said movement prevention means and to translate movement of said probe securing means in said first direction to said inner valve body for moving said inner valve body in said predetermined direction thereby to open the valve.

15. A valve as defined in claim 14, wherein said catch engagement means comprises a coil spring.

16. A valve as defined in claim 14, wherein said probe securing means comprises a hollow cylindrical cap threaded onto said inner valve body; and wherein said catch comprises at least one notch in said cap.

17. A valve as defined in claim 14, wherein said latching means includes means for latching said inner valve body in said open valve position.

18. A valve as defined in claim 17, wherein said latching means comprises a Z-shaped slot in said inner valve body and a guide pin mounted on said outer valve body for cooperation with said slot.

19. A safety valve for exposing a measuring probe to a fluid, comprising:

a hollow cylindrical outer valve body having a valve seat at one end;

a hollow cylindrical inner valve body positioned coaxially within said outer valve body and carrying a valve element at one end for cooperation with said valve seat, said inner valve body being closed at one end by a base so as to define an interior chamber and being open at the opposite end for receiving the probe, the cylindrical wall of said inner valve body adjacent said base having apertures for passage of fluid therethrough;

said inner valve body being movable within said outer valve body between open and closed valve positions, said inner valve body extending at least partially from said outer valve body in said open valve position for permitting passage of fluid through said apertures into said chamber for exposing the probe to the fluid, and said valve seat engaging said valve element in said closed valve position for blocking the passage of fluid into said chamber;

means for securing the probe in said inner valve body, said probe securing means being movable in a first direction for securing the probe and a second direction for releasing the probe;

means for closing the valve in response to movement of said probe securing means in said second direction so that said inner valve body moves to said closed position prior to removal of the probe; and lock means in the form of a spring wound around said inner valve body and operatively connected with said probe securing means and said outer valve body for exerting a biasing force preventing the valve from being opened in the absence of the probe, said lock means further restricting movement of said probe securing means in said second direction when the valve is in said open position to prevent the probe from being removed when the valve is open.

* * * * *